US008357799B2

(12) United States Patent (10) Patent No.: US 8,357,799 B2
Nazeeruddin et al. (45) Date of Patent: Jan. 22, 2013

(54) LIGHT EMITTING MATERIAL

(75) Inventors: Mohammad Khaja Nazeeruddin, Ecublens (CH); Nicholas Evans, London (GB); Michael Graetzel, Saint Sulpice (CH)

(73) Assignee: SOLVAY (Societe Anonyme), Brussels (BE)

( * ) Notice: Subject to any disclaimer, the term of this patent is extended or adjusted under 35 U.S.C. 154(b) by 416 days.

(21) Appl. No.: 12/602,811

(22) PCT Filed: Jun. 5, 2008

(86) PCT No.: PCT/EP2008/056953
§ 371 (c)(1),
(2), (4) Date: Dec. 3, 2009

(87) PCT Pub. No.: WO2008/148829
PCT Pub. Date: Dec. 11, 2008

(65) Prior Publication Data
US 2010/0190984 A1 Jul. 29, 2010

(30) Foreign Application Priority Data
Jun. 8, 2007 (EP) ..................................... 07109875

(51) Int. Cl.
C07F 15/00 (2006.01)
(52) U.S. Cl. .......................................................... 546/4
(58) Field of Classification Search ....................... 546/4
See application file for complete search history.

(56) References Cited

U.S. PATENT DOCUMENTS

| 6,670,645 | B2 | 12/2003 | Grushin et al. |
| 2005/0287391 | A1 | 12/2005 | Chang et al. |
| 2009/0115327 | A1 | 5/2009 | Nazeeruddin et al. |
| 2009/0200920 | A1 | 8/2009 | Jin et al. |

FOREIGN PATENT DOCUMENTS

| JP | 20030113163 A | 4/2003 |
| JP | 20030113164 A | 4/2003 |
| WO | WO 2007042474 A2 | 4/2007 |
| WO | WO 2007115972 A1 | 10/2007 |
| WO | WO 2008043815 A1 | 4/2008 |
| WO | WO 2008148830 A1 | 12/2008 |

OTHER PUBLICATIONS

Khan et al. "Synthesis and Characterization of Ru(II) and Ru(III) Complexes of Diphenylphosphinoacetic Acid and their Interaction with Small Molecules" Inorganica Chemica Acta, 1988, vol. 147, pp. 33-43.*
Dedeian et al. "A New Synthetic Route to the Preparation of a Series of Strong Photoreducing Agents: fac Tris-Ortho-Metalated Complexes of Iridium(III) with Substituted 2-Phenylpyridines" Inorganic Chemistry, 1991, vol. 30, pp. 1685-1687.*

M.A. Baldo et al. —"Very high-efficiency green organic light-emitting devices based on electrophosphorescence" —Applied Physics Letters 1999, vol. 75(1), p. 4-6.
M.M. Taqui Khan et al. —"Synthesis and characterization of platinum group metal complexes of diphenylphosphinoacetic acid" —Inorganica Chimica Acta, vol. 143 (1988), p. 177-184.
M.M. Taqui Khan et al. —"Synthesis and characterization of Ru(II) and Ru(III) complexes of diphenylphosphinoacetic acid and their interaction with small molecules" —Inorganica Chimica Acta, vol. 147 (1988), p. 33-43.
S.-M. Kuang et al. —"Complexes derived from the reaction of diphenylphosphinoacetic acid. Part 4 Mononuclear complexes of Rh(I), Ir(I), and Ir(III) and some related chemistry involving the diphenyl(2,6-dimethylphenyl)-phosphine ligand" —Inorganica Chimica Acta, vol. 343 (2003), p. 275-280.
T. Jarolim & J. Podlahova —"Coordinating behaviour of diphenylphosphineacetic acid" —J. inorg. Nucl Chem (1976), vol. 38, p. 125-129.
K. Dedeian et al. —"A new synthetic route to the preparation of a series of strong photoreducing agents : fac tris-ortho-matalated complexes of iridium (III) with substituted 2-phenylpyridines "—Inorg. Chem. 1991, vol. 30, p. 1685-1687.
F.O. Garces et al- "Synthesis, structure, electrochemistry and photophysics of methyl-substituted phenylpyridine ortho-metalated iridium (III) complexes" —Inorg. Chem. 1988, vol. 27, p. 3464-3471.
M.G. Colombo et al. —"Facial tris cyclometalated Rh(3+) and Ir(3+) complexes : their synthesis, structure and optical spectroscopic properties" —Inorg. Chem. 1994, vol. 33, p. 545-550.
J.H. Van Diemen et al. —"Synthesis, X-ray structure, electrochemical and electronic properties of [3-(pyridin-2yl)-4- methyl-1,2,4-triazole-bis-(2-(2'-phenylato)pyridine)-iridium(III)] hexafluorophosphate" —Inorganica Chimica Acta, vol. 181, (1991), p. 245-251.
J- Rohonczy et al. —"Trimethylsilylated N-alkyl-substituted carbamates III Structure of trimethylsilyl-N,N-diisopropyl carbamate in solid phase and in solution" —Journal of Organometallic Chemistry, vol. 340 (1988), p. 293-302.
K.A. King et al. —"Excited-state properties of a triply ortho-metalated iridium(III) complex" —J. Am. Chem. Soc., 1985, vol. 107, p. 1431-1432.
O. Lohse et al. —"The palladium catalyzed Suzuki coupling of 2- and 4-chloropyridines" —Synlett 1999, N°1, p. 45-48.
K. Issleib et al. —"Alkali-Phosphorverbindungen und ihr reaktives Verhalten V Darstellung von carboxyphosphinen R2P-[CH2]n-CO2H" —Chemische Berichte 1960, vol. 93, p. 803-808.

(Continued)

Primary Examiner — Joseph Kosack
(74) Attorney, Agent, or Firm — Foley & Lardner LLP (57) ABSTRACT

This invention pertains to light emitting materials comprising novel ortho-metalated transition metal complexes [C^N]$_2$M[P^O] comprising two orthometalated chelate C^N ligands and an ancillary ligand of bidentate phosphinocarboxylate type. It has been surprisingly found that when the metal has bound thereto both orthometalated chelate C^N ligands and an ancillary ligand of bidentate phosphinocarboxylate type (P^O), these ligands advantageously participate in the emission process, enabling appreciable improvement of the blue emission efficiency of complexes [C^N]$_2$M[P^O]. Still objects of the invention are the use of such light emitting materials and organic light emitting device comprising such light emitting material.

15 Claims, 2 Drawing Sheets

OTHER PUBLICATIONS

K.A. King & R.J. Watts —"Dual emission from an ortho-metalated Ir(III) complex "—J. am. Chem. Soc. 1987, vol. 109, p. 1589-1590.

D. Cuperly et al. —"First direct C-2-lithiation of 4-DMAP. Convenient access to reactive functional Derivatives and Ligands" —J. Org. Chem. 2002, vol. 67, p. 238-241.

G. Sanchez et al. —"Synthesis and haracterization of cyclometallated palladium(II) complexes with phosphine-carboxylate and phosphine-amie ligands" —Dalton Transactions 2003, vol. 24, p. 4709-4717.

U.S. Appl. No. 12/444,793, filed Apr. 8, 2007, Nazeeruddin et al.

U.S. Appl. No. 12/602,815. filed Dec. 3, 2009, Nazeeruddin et al.

* cited by examiner

LIGHT EMITTING MATERIAL

CROSS-REFERENCE TO RELATED APPLICATIONS

This application is a U.S. national stage application under 35 U.S.C. §371 of International Application No. PCT/EP2008/056953 filed Jun. 5, 2008, which claims priority to European Application No. 07109875.0 filed Jun. 8, 2007, these applications being incorporated herein by reference in their entirety for all purposes.

TECHNICAL FIELD

The present invention relates to a light-emitting material and the use of said material. The present invention further relates to a light-emitting device capable of converting electric energy to light.

BACKGROUND ART

Today, various display devices are being actively researched and developed, particularly those based on electroluminescence (EL) from organic materials.

Contrary to photoluminescence (i.e., light emission from an active material due to optical absorption and relaxation by radioactive decay of an excited state), electroluminescence (EL) refers to a non-thermal generation of light resulting from applying an electric field to a substrate. In the latter case, excitation is accomplished by recombining the charge carriers of contrary signs (electrons and holes) injected into an organic semiconductor in the presence of an external circuit.

A simple prototype of an organic light-emitting diode (OLED), i.e. a single layer OLED, is typically composed of a thin film made from an active organic material, which is sandwiched between two electrodes. One electrode needs to be semitransparent in order to observe the light emission from the organic layer. Typically, an indium tin oxide (ITO)-coated glass substrate is used as an anode.

If an external voltage is applied to the two electrodes, then the charge carriers (i.e., holes) at the anode and the electrons at the cathode are injected into the organic layer beyond a specific threshold voltage depending on the organic material applied. In the presence of an electric field, the charge carriers move through the active layer and are non-radioactively discharged when they reach the oppositely charged electrode. However, if a hole and an electron encounter one another while drifting through the organic layer, then excited singlet (anti-symmetric) and triplet (symmetric) states (so-called excitons) are formed. Light is thus generated in the organic material from the decay of molecular excited states (or excitons). For every three triplet excitons that are formed by electrical excitation in an OLED, only one symmetric state (singlet) exciton is created.

Many organic materials exhibit fluorescence (i.e., luminescence from a symmetry-allowed process) from singlet excitons, which may be efficient since this process occurs between states of same symmetry. On the contrary, if the symmetry of an exciton is different from the one of the ground state, then the radioactive relaxation of the exciton is disallowed and the luminescence will be slow and inefficient. Since the ground state is usually anti-symmetric, the decay from a triplet breaks symmetry. Thus, the process is disallowed and the efficiency of EL is very low. Therefore, the energy contained in the triplet states is mostly wasted.

Luminescence from a symmetry-disallowed process is known as phosphorescence. Typically, phosphorescence may last up to several seconds after excitation due to the low probability of the transition, which is different from fluorescence that originates in the rapid decay.

However, only a few organic materials have been identified, which show efficient room temperature phosphorescence from triplets.

If phosphorescent materials are successfully utilized, then this holds enormous promises and benefits for organic electroluminescent devices. For example, the advantage of utilizing phosphorescent materials is that all excitons (formed by combining holes and electrons in an EL), which are (in part) triplet-based in phosphorescent devices, may participate in energy transfer and luminescence. This can be achieved by phosphorescence emission itself. Alternatively, it can be accomplished by using phosphorescent materials for improving the efficiency of the fluorescence process as a phosphorescent host or a dopant in a fluorescent guest, with phosphorescence from a triplet state of the host enabling energy transfer from a triplet state of the host to a singlet state of the guest.

In every case, it is important that the light emitting material provides electroluminescence emission in a relatively narrow band centered near the selected spectral regions, which correspond to one of the three primary colours (red, green and blue). This is so that they may be used as a coloured layer in an OLED.

As a means for improving the properties of light-emitting devices, there has been reported a green light-emitting device utilizing the emission from ortho-metalated iridium complex. (Ir(ppy)3: tris-ortho-metalated complex of iridium (III) with 2-phenylpyridine (ppy). *Appl. phys. lett.* 1999, vol. 75, p. 4.

Thus, US 2005287391 (SAMSUNG SDI CO LTD) 29 Dec. 2005 discloses iridium(III) complexes, which emit light in the range from a blue region to a red region in a triplet metal-to-ligand charge transfer (MLCT) state, as represented by the following formulae 1 and 2:

[Formula 1]

wherein Q1 is an N-containing aromatic ring and Q2 is an aromatic ring fused to Q1;

Z is a carbonyl linking group (>C=), alkylene group, an oxygen linking group (—O—), a nitrogen atom linking group (—NH—), a thiocarbonyl linking group (>C=S), a sulfoxide linking group (>S=O), a sulfonyl linking group (—SO$_2$—) or a combination thereof.

[Formula 2]

wherein Q1' is an N-containing aromatic ring;
$m_1$ is an integer of 0 to 2 and $m_2$ is $3-m_1$; and
$R_1$, $R_2$, $R_3$, $R_4$, $R_5$, $R_6$, $R_7$ and $R_8$ are each a hydrogen or a substituent.

TAQUI KHAN, M. M., et al. Synthesis and characterization of platinum group metal complexes of diphenylphosphinoacetic acid. *Inorganica Chimica Acta*. 1988, vol. 143, p. 177-184. disclose that while interaction of POH (POH=diphenylphosphinoacetic acid) with Rh(I) and Ir(I) square planar complex MCl(CO)—(PPh$_3$)$_2$ in a 2:1 molar ratio gives complexes of the type trans-M(PO)(POH)(CO), interaction of RhCl$_3$ and IrCl$_3$ with POH in a 3:1 molar ratio results in the formation of complexes of the type M(PO)$_2$(POH)Cl (M=Rh(III) and Ir(III)).

TAQUI KHAN, M. M., et al. Synthesis and characterization of Ru(III) and Ru(II) complexes of diphenylphosphinacetic acid and their interaction with small molecules. *Inorganica Chimica Acta*. 1988, vol. 147, p. 33-43. also disclose that the ligand POH(POH=diphenylphosphinoacetic acid) reacts with RuCl$_2$-(PPh$_3$)$_3$ in a 3:1 molar ratio to provide a five-coordinate complex of composition Ru(PO)$_2$(POH) with complete displacement of PPh$_3$, but in a 2:1 molar ratio, the complex Ru(PO)$_2$(PPh$_3$) is formed.

KUANG, Shan-Ming, et al. Complexes derived from the reactions of diphenylphosphinoacetic acid. Part 4. Mononuclear complexes of Rh(I), Ir(I) and Ir(III) and some related chemistry involving the diphenyl(2,6-dimethylphenyl)-phosphine ligand. *Inorganica Chimica Acta*. 2003, vol. 343, p. 275-280. disclose the iridium(III) complex IrHCl(CO)($\eta^2$-Ph$_2$PCH$_2$CO$_2$)($\eta^1$-Ph$_2$PCH$_2$CO$_2$H) prepared by reacting the iridium complex [IrCl(COD)]$_2$ with diphenylphosphinoacetic acid in the presence of CO, which in the solid state exists as a hydrogen-bonded dimmer.

JAROLIM, T., et al. Coordinating behaviour of diphenylphosphinoacetic acid. *J. Inorg. Nucl. Chem.* 1976, vol. 38, p. 125-129. disclose diphenylphosphineacetic acid as a versatile ligand, which exists in three coordination modes of the bonding through carbonyl alone; the chelate-forming ligand coordinated through both phosphorous and carbonyl; and the bonding through phosphorous alone.

However, since the foregoing light-emitting materials of the prior art do not display pure colours, i.e., their emission bands, generally limited to green, are not centered near selected spectral regions, which correspond to one of the three primary colours (red, green and blue), the range within them can be applied as OLED active compound is narrow. It has thus been desired to develop light-emitting materials capable of emitting light having other colours, especially in the blue region.

Efficient long-lived blue-light emitters with good colour coordinates are a recognized current shortfall in the field of organic electroluminescent devices.

DISCLOSURE OF INVENTION

It is thus an object of the present invention to provide a light emitting material comprising a neutral ortho-metalated complex having ancillary ligands, as shown below.

It is another object of the present invention to use said light emitting material and an organic light emitting device comprising said light emitting material.

The first object of the present invention is to provide a light emitting material comprising a neutral complex of formula (I):

wherein:
M represents a transition metal of atomic number of at least 40, preferably of groups 8 to 12, more preferably Ir or Pt, most preferably Ir;

$E_1$ represents an aromatic or heteroaromatic ring, optionally condensed with additional aromatic moieties or non aromatic cycles, said ring optionally having one or more substituents, optionally forming a condensed structure with the ring comprising $E_2$, said ring coordinating to the metal M via a sp$^2$ hybridized carbon;

$E_2$ represents a N-containing aromatic ring, optionally condensed with additional aromatic moieties or non aromatic cycles, said ring optionally having one or more substituents, optionally forming a condensed structure with the ring comprising $E_1$, said ring coordinating the metal M via a sp$^2$ hybridized nitrogen; and $X_1$ and $X_2$ are same or different at each occurrence and are independently selected among alkyl, aryl, heteroaryl and alkyl, each of which may be substituted by at least one substituent.

The two chelating monoanionic ligands bound to the metal through a carbon and a nitrogen atom as specified in formula (I), comprising $E_1$ and $E_2$ moieties, are generally denoted as orthometalated ligands (C^N ligands, hereinafter).

The chelating bidentate phosphinocarboxylate monoanionic ligand bound to the metal through an oxygen and a phosphorous atom is generally denoted as ancillary ligand (P^O ligand).

Surprisingly, it has been found that when the metal binds both orthometalated ligands comprising $E_1$ and $E_2$ moieties and an ancillary ligand of bidentate phosphinocarboxylate type, said ligands advantageously participate in the emission process, thereby significantly improving the blue emission efficiency of complexes [C^N]$_2$M[P^O].

Neutral complexes complying with formula (I) are also preferred over ionic (cationic or anionic) complexes since they are generally less sensitive to moisture and can be advantageously sublimated throughout purification.

The chelate bidentale phosphinocarboxylate monoionic ligand generally forms with the central transition metal atom, a 5-membered, 6-membered or 7-membered metalacycle, that is to say that the phosphino group and the carboxylate moiety can be separed notably by one, two or three carbon atoms.

Preferred P^O ligands are those wherein the phosphino group and the carboxylate group are bound to the same carbon atom: these ligands advantageously form complexes comprising a 5-membered metalacycle, particularly stable.

Preferably, the light emitting material of the present invention comprises a neutral complex of formula (II):

(II)

wherein:
X$_1$ and X$_2$ have the same meaning as defined above;

X is chosen from the group consisting of —CH=CH—, —CR=CH—, —CR=CR—, N—H, N—R$^1$, O, S and Se; X is preferably selected from —CH=CH—, —CR=CH— and S; X is most preferably —CH=CH—;

Y is chosen from the group consisting of —CH=CH—, —CR=CH—, —CR=CR—, N—H, N—R$^1$, O, S and Se; Y is preferably selected from —CH=CH—, —CR=CH— and S; Y is most preferably —CH=CH—;

R is same or different at each occurrence and is —F, —Cl, —Br, —NO$_2$, —CN; a straight-chain or branched or cyclic alkyl or alkoxy group or dialkylamino group having 1 to 20 carbon atoms, each of which one or more nonadjacent —CH$_2$— groups may be replaced by —O—, —S—, —NR$^1$— or —CONR$^2$—, and each of which one or more hydrogen atoms may be replaced by F; an aryl or heteroaryl group having 4 to 14 carbon atoms which may be substituted by one or more non aromatic radicals; and a plurality of substituents R, either on the same ring or on the two different rings, may in turn form together a further mono- or polycyclic ring system, optionally aromatic;

R$^1$ and R$^2$ are same or different at each occurrence, and each H or an aliphatic or aromatic hydrocarbon radical has 1 to 20 carbon atoms;

a is an integer from 0 to 4; and b is an integer from 0 to 4.

More preferably, the light emitting material of the present invention comprises a neutral complex of formula (IIA):

(IIA)

wherein:
X$_1$, X$_2$, Y, X and a have the same meaning as defined above;
R$_A$ and R$_B$, are same or different at each occurrence and are independently selected among —F, —Cl, —Br, —NO$_2$, —CN; a straight-chain or branched or cyclic alkyl or alkoxy group having from 1 to 20 carbon atoms, each of which one or more nonadjacent —CH$_2$— groups may be replaced by —O—, —S—, —NR$^1$—, or —CONR$^2$—, and each of which one or more hydrogen atoms may be replaced by F; an aryl or heteroaryl group having 4 to 14 carbon atoms which may be substituted by one or more non aromatic radicals; and a plurality of substituents R$_A$ and/or R$_B$, either on the same ring or on the two different rings, may in turn form together a further mono- or polycyclic ring system, optionally aromatic; preferably R$_A$ and/or R$_B$ are fluorine groups (—F);

R$^x$ and R$^y$ are same or different at each occurrence and are independently chosen among C$_1$-C$_6$ alkyl, fluoro- or perfluoroalkyl groups, e.g. —CH$_3$, -nC$_4$H$_9$, -iC$_3$H$_7$, —CF$_3$, —C$_2$F$_5$, —C$_3$F$_7$ or C$_1$-C$_6$ alkyl, fluoro- or perfluoroalkyl groups having one or more ether groups; preferably R$^x$ and R$^y$ are independently chosen among C$_1$-C$_6$ alkyl groups; more preferably R$^x$ and R$^y$ being selected from methyl, ethyl, n-propyl, i-propyl, n-butyl groups, R$^1$ and R$^2$ are same or different at each occurrence, each H or an aliphatic or aromatic hydrocarbon radical having 1 to 20 carbon atoms;

b is an integer from 0 to 3; and w is an integer between 1 and 4.

Particularly preferred complexes of formula (IIA) are those wherein at least one dialkylamino group —NR$^x$R$^y$ is located in the para position with respect to the nitrogen atom.

Among the complexes of the present invention, the preferred ones are those wherein X$_1$ and X$_2$ are each independently selected from unsubstituted or substituted aryl groups.

More preferred are those wherein X$_1$ and X$_2$ are phenyl.

Excellent results were obtained with light emitting materials comprising a neutral complex of formula (III) to (V):

(III)

(IV)

(V)

Neutral complexes of formulas (III) to (V) comprising orthometalated ligands and a diphenylphosphino acetate moiety as ancillary ligand are particularly advantageous for the purposes of this invention due to their emission in the blue region with high colour purity.

Best results have been obtained with complex (III), as above detailed, wherein a dimethylamino substituent is present in the para-position with respect to the nitrogen of the phenyl-pyridine ligand.

The diphenylphosphino fraction of the bidentate P^O ligand advantageously acts as an optimal π-acid that stabilizes Ir HOMO orbitals, whereas carboxylate group of P^O ligand advantageously counteracts the positive charge on metal resulting in neutral complex. Thus, the P^O ligand has been advantageously found to maintain a fine balance of electron density upon coordination to platinum group metals.

The synthesis of complexes of formula (I), i.e., metal complex comprising two orthometalated ligands (C^N ligands) and a bidentate phosphinoacetate ligand (P^O), can be accomplished by any known method. The details of synthetic methods suitable for the preparation of complexes of formula (I) are disclosed in "Inorg. Chem.", No. 30, pg. 1685 (1991); "Inorg. Chem.", No. 27, pg. 3464 (1988); "Inorg. Chem.", No. 33, pag. 545 (1994); "Inorg. Chem. Acta", No. 181, pag. 245 (1991), "J. Organomet. Chem.", No. 35, pg. 293 (1987), "J. Am. Chem. Soc.", No. 107, pg. 1431 (1985).

Generally, according to the first embodiment, the complexes complying with formula (I) can be prepared according to the following reaction scheme

The acid forms of the orthometalated ligands (H—C^N) and ancillary ligands (P^O—H) can be commercially available or easily synthesized by well-known organic synthesis reaction pathways.

In particular, orthometalated ligands (H—C^N) can be prepared with good to excellent yields by using the Suzuki coupling of the substituted pyridine compound with corresponding arylboronic acids, as described in LOHSE, Olivier, et al. The Palladium Catalyzed Suzuki Coupling of 2- and 4-chloropyridines. *Syn. Lett.* 1999, no. 1, p. 15-18. and in U.S. Pat. No. 6,670,645 (DU PONT DE NEMOURS) 30 Dec. 2003.

Synthetic methods, which are particularly adapted for the preparation of fluorinated orthometalated ligands (H—C^N), are described in JP 2003113164 A (MITSUBISHI MATERIALS CORP) 18 Apr. 2003 and in JP 2003113163 A (MITSUBISHI MATERIALS CORP) 18 Apr. 2003.

If the transition metal is iridium, trihalogenated iridium (III) compounds such as $IrCl_3.H_2O$, hexahalogenated iridium (III) compounds such as $M°_3 IrX°_6$, wherein $X°$ is a halogen, preferably Cl and $M°$ is an alkaline metal, preferably K, and hexahalogenated iridium (IV) compounds such as $M°_2 IrX°_6$, wherein $X°$ is a halogen, preferably Cl and $M°$ is an alkaline metal, preferably K (Ir halogenated precursors) can be used as starting materials to synthesize the complexes of formula (I).

Further, phosphinoacetate ligand (P^O—H) such as diphenylphosphino acetic acid can be synthesized in three steps, which is described in the literatures [K. Issleib and G. Thomas, *Ber.*, 93, 803, 1960; T. Jarolim and J. Podlahova, *J. Inorg. Nucl. Chem.*, 38, 125, 1976], as shown in the following scheme:

$[C^N]_2Ir(\mu-X°)_2Ir[C^N]_2$ complexes (compound VIII, wherein M=Ir), with $X°$ being a halogen, preferably Cl (e.g., $[(2-(2,4-difluorophenyl)-4-dimethylaminopyridine)_2IrCl]_2$, $[(2-(2,4-difluorophenyl)pyridine)_2IrCl]_2$, $[(2-phenylpyridine)_2IrCl]_2$ and $[(2-(2,4-difluorophenyl)-5-dimethylaminopyridine)_2IrCl]_2$) can be prepared from said Ir halogenated precursors and the appropriate orthometalated ligand by resorting to literature procedures ([King, K. A.; Watts, R. J. *J. Am. Chem. Soc.* 1987, 109, 1589-1590]).

Reaction is advantageously carried out by using an excess of the neutral form of the orthometalated ligand (H—C^N). High boiling temperature solvents are preferred.

For purposes of the present invention, the term high-boiling temperature solvent is intended to denote a solvent having a boiling point of at least 80° C., preferably of at least 85° C., more preferably of at least 90° C. Suitable solvents are, for example, methoxyethanol, ethoxyethanol, glycerol, dimethylformamide (DMF), N-methylpyrrolidone (NMP), dimethylsulfoxide (DMSO) and the like. Said solvents can be used as such or in admixture with water.

Optionally, reaction can be carried out in the presence of a suitable Brønsted base such as metal carbonates, particularly potassium carbonate ($K_2CO_3$), metal hydrides, particularly sodium hydride (NaH), metal ethoxide or metal methoxide, particularly $NaOCH_3$, $NaOC_2H_5$, alkylammonium hydroxides, particularly tetramethylammonium hydroxide, or imidazolium hydroxides.

A nucleophilic substitution at the metal atom with a suitable ligand (P^O), as defined above for forming corresponding [C^N]$_2$Ir[P^O] (formula I, wherein Me=Ir here above), is advantageously carried out by roughly contacting a stoichiometric amount of ligand P^O—H with a bridged intermediate (VIII) in a suitable solvent.

Polar aprotic solvents are generally preferred for this reaction. A solvent, which gives particularly good results, is methylene dichloride ($CH_2Cl_2$).

The present invention is also directed to using the light emitting material, which is described above, in the emissive layer of an organic light emitting device (OLED).

Furthermore, the present invention is directed to using the light emitting material, which is defined above, as a dopant in a host layer, thus functioning as an emissive layer in an organic light emitting device.

If the light emitting material is used as a dopant in a host layer, it is generally used in an amount of at least 1% wt, preferably of at least 3% wt, more preferably of least 5% wt with respect to the total weight of the host and the dopant, and generally at most 25% wt, preferably at most 20% wt, more preferably at most 15% wt.

The present invention is also directed to an organic light emitting device (OLED) comprising an emissive layer (EML). The emissive layer comprises the light emitting material, which is described above, optionally with a host material (wherein the light emitting material is preferably present as a dopant). The host material is notably adapted to luminesce when a voltage is applied across the device structure.

The OLED generally comprises:
a glass substrate;
an anode, which is a generally transparent anode such as an indium-tin oxide (ITO) anode;
a hole transporting layer (HTL);
an emissive layer (EML);
an electron transporting layer (ETL); and
a cathode, which is generally a metallic cathode such as an Al layer.

As for a hole conducting emissive layer, one may have an exciton blocking layer, notably a hole blocking layer (HBL) between the emissive layer and the electron transporting layer. As for an electron conducting emissive layer, one may have an exciton blocking layer, notably an electron blocking layer (EBL) between the emissive layer and the hole transporting layer. The emissive layer may be equal to the hole transporting layer (in which case the exciton blocking layer is near or at the anode) or to the electron transporting layer (in which case the exciton blocking layer is near or at the cathode).

The emissive layer may be formed with a host material in which the above-described light emitting material resides as a guest or the emissive layer may consist essentially of the light emitting material. In the former case, the host material may be a hole-transporting material selected from the group of substituted tri-aryl amines. Preferably, the emissive layer is formed with a host material in which the light emitting material resides as a guest. The host material may be an electron-transporting material selected from the group consisting of metal quinoxolates (e.g., aluminium quinolate ($Alq_3$), lithium quinolate (Liq)), oxadiazoles and triazoles. An example of a host material is 4,4'-N,N'-dicarbazole-biphenyl ["CBP"], which has the following formula:

CBP

Optionally, the emissive layer may also contain a polarization molecule, which is present as a dopant in said host material and having a dipole moment, that generally affects the wavelength of light emitted when said light emitting material used as a dopant luminesces.

A layer formed of an electron transporting material is advantageously used to transport electrons into the emissive layer comprising the light emitting material and the (optional) host material. The electron transporting material may be an electron-transporting matrix selected from the group consisting of metal quinoxolates (e.g., $Alq_3$, Liq), oxadiazoles and triazoles. An example of an electron transporting material is tris-(8-hydroxyquinoline)aluminium of formula ["$Alq_3$"]:

$Alq_3$

A layer formed of a hole transporting material is advantageously used to transport holes into the emissive layer comprising the above-described light emitting material and the (optional) host material. An example of a hole transporting material is 4,4'-bis[N-(1-naphthyl)-N-phenylamino]biphenyl ["α-NPD"].

α-NPD

The use of an exciton blocking layer ("barrier layer") to confine excitons within the luminescent layer ("luminescent zone") is greatly preferred. As for a hole-transporting host, the blocking layer may be placed between the emissive layer and the electron transport layer. An example of a material, which is used for such a barrier layer, is 2,9-dimethyl-4,7-diphenyl-1,10-phenanthroline (also called bathocuproine or "BCP") having the following formula:

BCP

Figure 1:
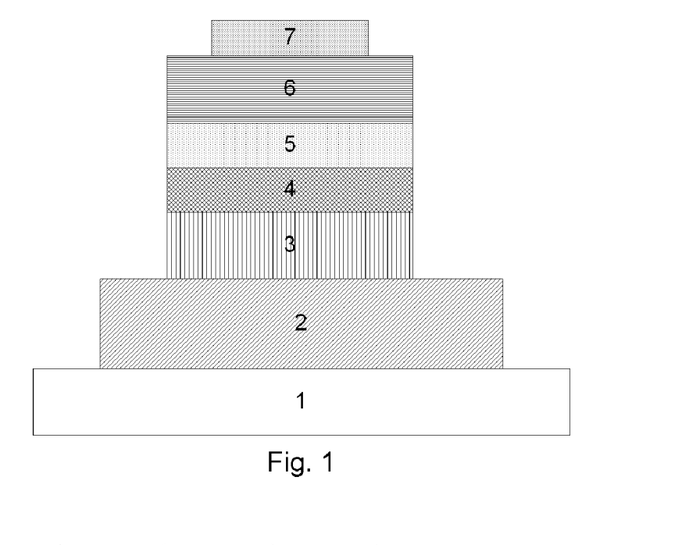

The OLED preferably has a multilayer structure, as depicted in FIG. 1, wherein: 1 is a glass substrate; 2 is an ITO layer; 3 is a HTL layer comprising α-NPD; 4 is an EML comprising CBP as a host material and the light emitting material as a dopant in an amount of about 8% wt with respect to the total weight of host and dopant; 5 is a HBL comprising BCP; 6 is an ETL comprising Alq$_3$; and 7 is an Al layer cathode.

EXAMPLES

Synthesis of 2-iodo-4-dimethylaminopyridine

BF$_3$.Et$_2$O (8.4 g, 59 mmol) was added dropwise to a solution of 4-dimethylaminopyridine (6 g, 49 mmol) in dry THF (250 ml) at 0° C. The resulting mixture was stirred for 1 hour at 0° C. under nitrogen. Temperature was cooled down to −78° C. and BuLi (1.6 M in hexane, 46 ml, 74 mmol) was added dropwise. The resulting mixture was stirred for 1 hour at −78° C. and a solution of I$_2$ (18.7 g, 74 mmol) in dry THF (50 ml) was added dropwise. The resulting mixture was stirred at −78° C. for 2 hours and allowed to warm to room temperature (2 hours). THF was evaporated and a saturated Na$_2$S$_2$O$_5$ solution was added. The resulting slurry was extracted with EtOAc (5×150 ml). The combined organic fractions were successively washed with saturated Na$_2$S$_2$O$_5$ (50 ml), brine (50 ml), dried over MgSO$_4$, filtered and evaporated to dryness. The resulting residue was purified by chromatography column (SiO$_2$, EtOAc/petroleum ether, 1/1) to afford 7 g (57%) of the desired compound as colourless oil, which solidified upon standing.

$^1$H and $^{13}$C NMR agreed with those reported in the literature (Cuperly, D.; Gros, P.; Fort, Y. *J. Org. Chem.* 2002, 67, 238-241).

Synthesis of 2-(2,4-difluorophenyl)-4-dimethylaminopyridine

A mixture of 2-iodo-4-dimethylaminopyridine (3 g, 12 mmol), 2,4-difluorophenylboronic acid (2.3 g, 14.5 mmol) and K$_2$CO$_3$ (6 g, 43.5 mmol) in toluene (60 ml) and water (10 ml) were degassed with nitrogen for 15 minutes. Pd(PPh$_3$)$_4$ (800 mg, 0.66 mmol) was added and the resulting mixture was heated to 90° C. for 48 hours under nitrogen. After being cooled to room temperature, the aqueous phase was separated and extracted with EtOAc (3×100 ml). The combined organic fractions were washed with brine, dried over MgSO$_4$, filtered and evaporated. To further purify the compound, the so-obtained oil was dissolved in Et$_2$O and extracted with 10% HCl solution (3×50 ml). The combined aqueous fractions were washed with Et$_2$O (2×100 ml) and neutralized with concentrated NaOH aqueous solution. The resulting mixture was extracted with EtOAc (4×100 ml), the combined organic fractions were washed with brine (50 ml), dried over MgSO4, filtered and evaporated to dryness. The crude compound was purified by column chromatography (SiO$_2$, CHCl$_3$ then CHCl$_3$/MeOH, 97/3) to afford 2.2 g (78%) of the titled compound as slightly yellow oil, which solidified upon standing.

$^1$H-NMR (CDCl$_3$, 298K, 200 MHz, δ ppm) 3.05 (s, 6H), 6.49 (dd, J=2.5 and 6 Hz, 1H), 6.92 (m, 3H), 7.94 (m, 1H), 8.33 (d, J=6 Hz, 1H).

Synthesis of [(2-(2,4-difluorophenyl)-4-dimethylaminopyridine)$_2$IrCl]$_2$ 2.5 equivalents of 2-(2,4-difluorophenyl)-4-dimethylaminopyridine and 1 equivalent of IrCl$_3$.3H$_2$O were heated at 110° C. in a mixture of 2-ethoxyethanol and water (3/1, v/v) for 15 hours under nitrogen. After being cooled to room temperature, the resulting precipitate was filtered off, successively washed with methanol than Et$_2$O and dried to afford the desired dimer. Because of the low solubility of this compound, its $^1$H-NMR was recorded in DMSO-d$^6$ as its [C^N]$_2$Ir(Cl)(DMSO) derivative.

$^1$H-NMR (DMSO-d$^6$, 298K, 200 MHz, δ ppm) 3.16 (s, 6H), 3.19 (s, 6H), 5.35 (dd, J=2 and 8.7 Hz, 1H), 5.83 (dd, J=2 and 8.7 Hz, 1H), 6.70-7.00 (m, 4H), 7.37 (m, 2H), 8.86 (d, J=7 Hz, 1H), 9.21 (d, J=7 Hz, 1H).

[(2-(2,4-difluorophenyl)pyridine)$_2$IrCl]$_2$, [(2-phenylpyridine)$_2$IrCl]$_2$ and [(2-(2,4-difluorophenyl)-5-dimethylaminopyridine)$_2$IrCl]$_2$ were prepared analogously as described above.

Synthesis of [(2-(2,4-difluorophenyl)-4-dimethylaminopyridine)$_2$ Ir(diphenylphosphinoacetate) [complex (III)]

[(2-(2,4-difluorophenyl)-4-dimethylaminopyridine)$_2$IrCl]$_2$ (91 mg, 0.065 mmol), diphenylphosphinoacetic acid (41 mg, 0.168 mmol), and tetrabutylammoniumhydroxide 30 hydrate (135 mg 0.168 mmol) were refluxed in CH$_2$Cl$_2$ (100 ml) for 6 hours under argon. There was some insoluble black precipitate, which was filtered and the solvent CH$_2$Cl$_2$ was evaporated. The resulting yellow oily substance was dissolved in 3 mL of C$_2$H$_5$OH and crystallized by slow diffusion of diethyl ether. The light yellow precipitate was filtered, washed with Et$_2$O and air dried to afford 45 mg (yield, 50%).

Figure 2:
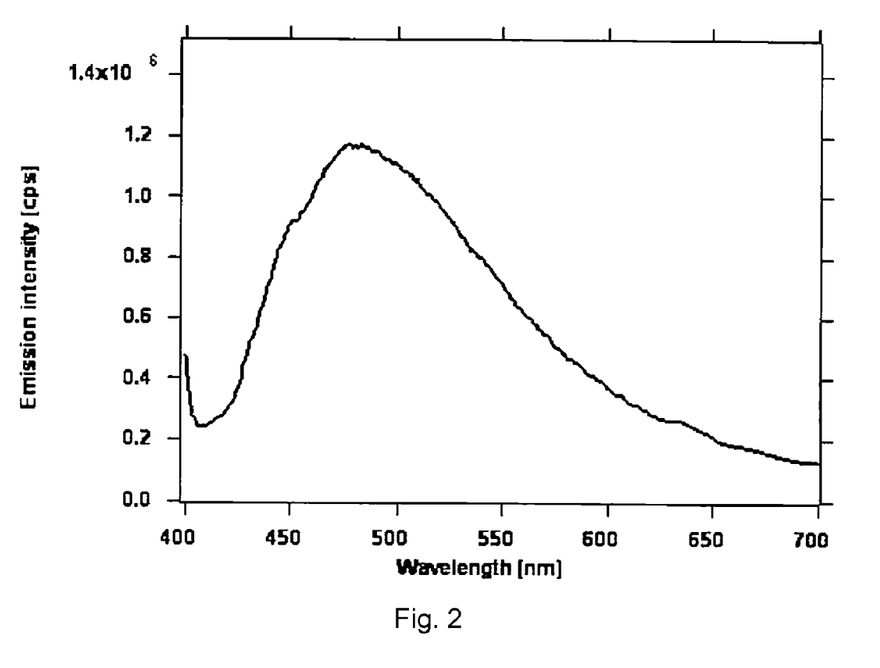

FIG. 2 shows the emission spectra registered from a complex (III) solution in dichloromethane at 298 K by excitation at 380 nm. The abscissa stands for the wavelength in nm and the ordinate stands for the emission intensity (cps).

Synthesis of [(2-(2,4-difluorophenyl)pyridine)$_2$Ir (diphenylphosphinoacetate) [complex (IV)]

[(2-(2,4-difluorophenyl)-pyridine)$_2$IrCl]$_2$ (63 mg, 0.051 mmol), diphenylphosphinoacetic acid (32 mg, 0.131 mmol) and tetrabutylammoniumhydroxide 30 hydrate (105 mg 0.131 mmol) were refluxed in CH$_2$Cl$_2$ (100 ml) for 6 hours under argon. After evaporation of the solvent, the resulting yellow solid was dissolved in 3 mL of C$_2$H$_5$OH. The obtained solution was left at room temperature for 24 hours resulting in nice crystalline solid. The light yellow crystals were filtered, washed with Et$_2$O and air dried to afford 40 mg of the desired complex (yield: 82%).

Figure 3:
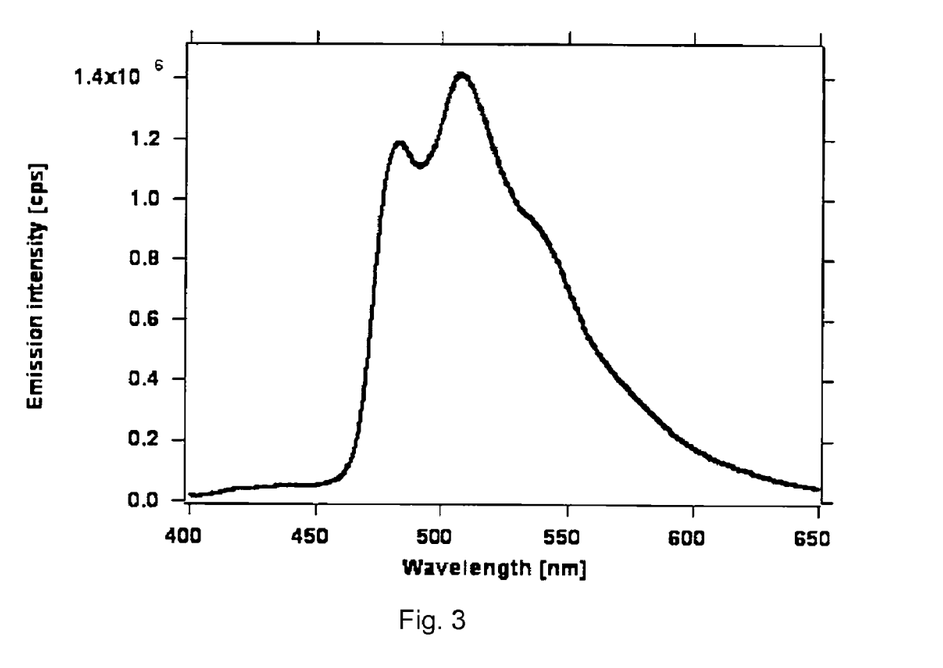

FIG. 3 shows the emission spectra registered from a complex (IV) solution in dichloromethane at 298 K by excitation at 400 nm. The abscissa stands for the wavelength in nm and the ordinate stands for the emission intensity (cps).

Synthesis of [(2-phenylpyridine)$_2$Ir(diphenylphosphinoacetate) [complex (V)]

[(2-(phenyl)pyridine)$_2$IrCl]$_2$ (56 mg, 0.052 mmol), diphenylphosphinoacetic acid (30 mg, 0.123 mmol) and tetrabutylammoniumhydroxide 30 hydrate (100 mg 0.125 mmol) were refluxed in CH$_2$Cl$_2$ (60 ml) for 5 hours under argon. After evaporation of the solvent, the resulting yellow solid was dissolved in 3 mL of CH$_3$OH. The obtained solution was left at room temperature for 24 hours resulting in nice crystalline solid. The light yellow crystals were filtered, washed with Et$_2$O and air dried to afford 27 mg of the desired complex (yield: 77%).

Figure 4:
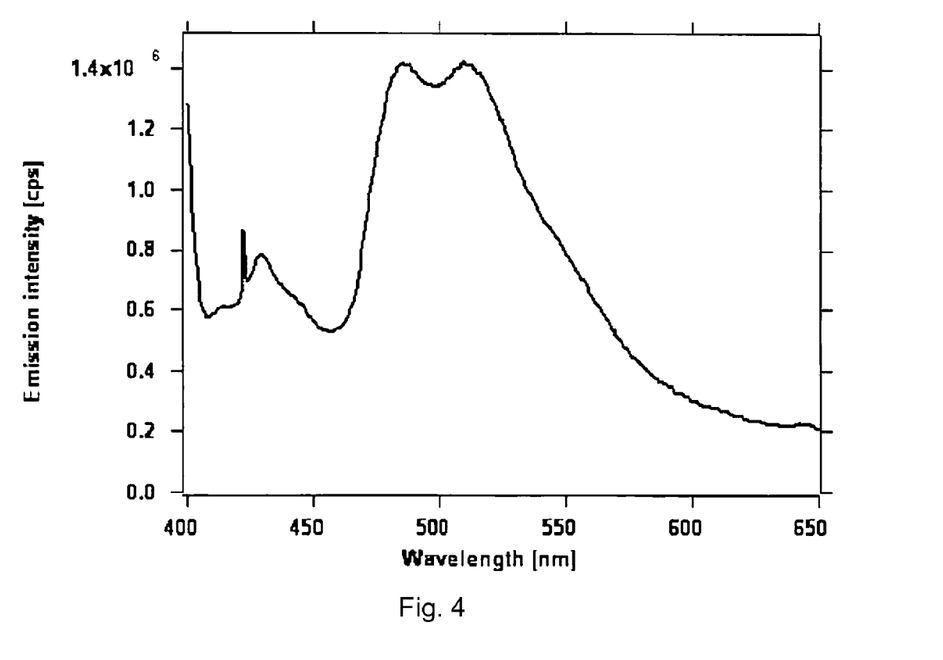

FIG. 4 shows the emission spectra registered from a complex (V) solution in dichloromethane at 298 K by excitation at 380 nm. The abscissa stands for the wavelength in nm and the ordinate stands for the emission intensity (cps).

Table 1 summarizes the emission properties of the iridium neutral complexes (III), (IV), and (V).

TABLE 1

Emission properties of the complexes (III), (IV), and (V), measured in dichloromethane

| Complex | Emission ($\lambda_{max}$) |
| --- | --- |
| (III) | 451, 478 |
| (IV) | 461, 490 |
| (V) | 485, 510 |

The invention claimed is:

1. A neutral complex of formula:

(I)

wherein:
M represents a transition metal of atomic number of at least 40;
E$_1$ represents an aromatic or heteroaromatic ring, optionally condensed with additional aromatic moieties or non aromatic cycles, said ring optionally having one or more substituents, optionally forming a condensed structure with the ring comprising E$_2$, said ring coordinating to the metal M via a sp$^2$ hybridized carbon;
E$_2$ represents a N-containing aromatic ring, optionally condensed with additional aromatic moieties or non aromatic cycles, said ring optionally having one or more substituents, optionally forming a condensed structure with the ring comprising E$_1$, said ring coordinating the metal M via a sp$^2$ hybridized nitrogen; and
X$_1$ and X$_2$ are same or different at each occurrence and are independently selected from the group consisting of alkyl, aryl, heteroaryl, and alkyl, each of which is optionally substituted by at least one substituent, wherein the phosphino group and the carboxylate moiety illustrated in Formula (I) are separated by one, two, or three carbon atoms.

2. The neutral complex of claim 1, represented by formula (II):

(II)

wherein:
X$_1$ and X$_2$ have the same meaning as defined in claim 1;
X is selected from the group consisting of —CH═CH—, —CR═CH—, —CR═CR—, N—H, N—R$^1$, O, S, and Se;
Y is selected from the group consisting of —CH═CH—, —CR═CH—, —CR═CR—, N—H, N—R$^1$, O, S, and Se;
R is same or different at each occurrence and is selected from the group consisting of —F, —Cl, —Br, —NO$_2$ —CN; a straight-chain or branched or cyclic alkyl or alkoxy group or dialkylamino group having 1 to 20 carbon atoms, each of which one or more nonadjacent —CH$_2$— groups is optionally replaced by —O—, —S—, —NR$^1$— or —CONR$^2$—, and each of which one or more hydrogen atoms is optionally replaced by. F; and an aryl or heteroaryl group having 4 to 14 carbon atoms which is optionally substituted by one or more non aromatic radicals; and
wherein optionally a plurality of substituents R, either on the same ring or on the two different rings, in turn form together a further mono- or polycyclic ring system, optionally aromatic;
R$^1$ and R$^2$ are same or different at each occurrence, and each being H or an aliphatic or aromatic hydrocarbon radical has 1 to 20 carbon atoms;
a is an integer from 0 to 4; and
b is an integer from 0 to 4.

3. The neutral complex of claim 2, represented by formula (IIA):

(IIA)

wherein:
X$_1$, X$_2$, Y, X and a have the same meaning as defined in claim 2;

$R_A$ and $R_B$, are same or different at each occurrence and are independently selected from the group consisting of —F, —Cl, —Br, —$NO_2$, —CN; a straight-chain or branched or cyclic alkyl or alkoxy group having from 1 to 20 carbon atoms, each of which one or more nonadjacent —$CH_2$— groups is optionally replaced by —O—, —S—, —$NR^1$ or $CONR^2$—, and each of which one or more hydrogen atoms is optionally replaced by F; and an aryl or heteroaryl group having 4 to 14 carbon atoms which is optionally substituted by one or more non aromatic radicals; and wherein optionally a plurality of substituents $R_A$ and/or $R_B$, either on the same ring or on the two different rings, in turn form together a further mono- or polycyclic ring system, optionally aromatic;

$R^X$ and $R^Y$ are same or different at each occurrence and are independently selected from the group consisting of $C_1$-$C_6$ alkyl groups, $C_1$-$C_6$ fluoroalkyl groups, $C_1$-$C_6$ perfluoroalkyl groups, and $C_1$-$C_6$ alkyl, fluoro- or perfluoroalkyl groups having one or more ether groups;

$R^1$ and $R^2$ are same or different at each occurrence, each being H or an aliphatic or aromatic hydrocarbon radical having 1 to 20 carbon atoms;

b is an integer from 0 to 3; and w is an integer between 1 and 4.

4. The complex according to claim 1, wherein $X_1$ and $X_2$ are, each independently selected from the group consisting of unsubstituted aryl groups and substituted aryl groups.

5. The complex according to claim 4, wherein both $X_1$ and $X^2$ are phenyl.

6. The complex according to claim 3, represented by formula (III):

(III)

7. The complex according to claim 1, represented by formula (IV):

(IV)

8. The complex according to claim 1, represented by formula (V):

(V)

9. A light emitting material comprising the complex according to claim 1.

10. A method for forming an emissive layer of an organic light emitting device, comprising using the light emitting material according to claim 9 in the emissive layer.

11. A method for forming an emissive layer of an organic light emitting device, comprising using the light emitting material according to claim 9 as a dopant in a host layer, thereby functioning as the emissive layer in the organic light emitting device.

12. An organic light emitting device (OLED) comprising an emissive layer (EML), wherein said emissive layer comprises the light emitting material according to claim 9, and optionally a host material.

13. A display device comprising the organic light emitting device according to claim 12.

14. The neutral complex of claim 1, wherein the phosphino group and the carboxylate moiety illustrated in Formula (I) are separated by one carbon atom.

15. The neutral complex of claim 1, wherein the phosphino group and the carboxylate moiety illustrated in Formula (I) are separated by two or three carbon atoms.

* * * * *